United States Patent [19]

Skwor

[11] Patent Number: 4,500,025
[45] Date of Patent: Feb. 19, 1985

[54] BONE STAPLER

[75] Inventor: Edward P. Skwor, Burnsville, Minn.

[73] Assignee: Minnesota Mining and Manufacturing Company, St. Paul, Minn.

[21] Appl. No.: 514,929

[22] Filed: Jul. 18, 1983

[51] Int. Cl.³ .............................................. A61B 17/04
[52] U.S. Cl. ................................ 227/19; 227/DIG. 1; 227/109; 227/121; 227/156; 128/334 R
[58] Field of Search ............. 128/334 R; 227/DIG. 1, 227/8, 19, 120, 130, 156, 121, 109

[56] References Cited

U.S. PATENT DOCUMENTS

| | | | |
|---|---|---|---|
| 3,087,160 | 4/1963 | Doppelt | 227/130 |
| 3,717,294 | 2/1973 | Green | 227/19 |
| 4,204,623 | 5/1980 | Green | 227/19 |
| 4,256,251 | 5/1981 | Moshofsky | 227/120 |
| 4,263,903 | 4/1981 | Griggs | 227/147 X |
| 4,412,539 | 11/1983 | Jaruik | 227/DIG. 1 X |
| 4,414,967 | 11/1983 | Shapiro | 227/DIG. 1 X |
| 4,415,111 | 11/1983 | McHarrie et al. | 227/19 |

Primary Examiner—Paul A. Bell
Attorney, Agent, or Firm—Donald M. Sell; James A. Smith; William L. Huebsch

[57] ABSTRACT

A bone stapler including a housing in which stapler can be driven by a driver along a passageway from an inlet to an outlet opening by activation of an operated drive means. Pointed projections are provided to locate bone portions to be stapled, manually releasable safety means is provided to prevent inadvertent driving of a staple, and the drive means is adapted to exhaust air at a location remote from the bone portion being stapled. Also a staple cartridge is provided that, when removed from the stapler, insures that no staple can remain in the stapler, and the stapler will accept different parts that receive the cartridge and define the passageway so that staples of different sizes may be driven.

1 Claim, 12 Drawing Figures

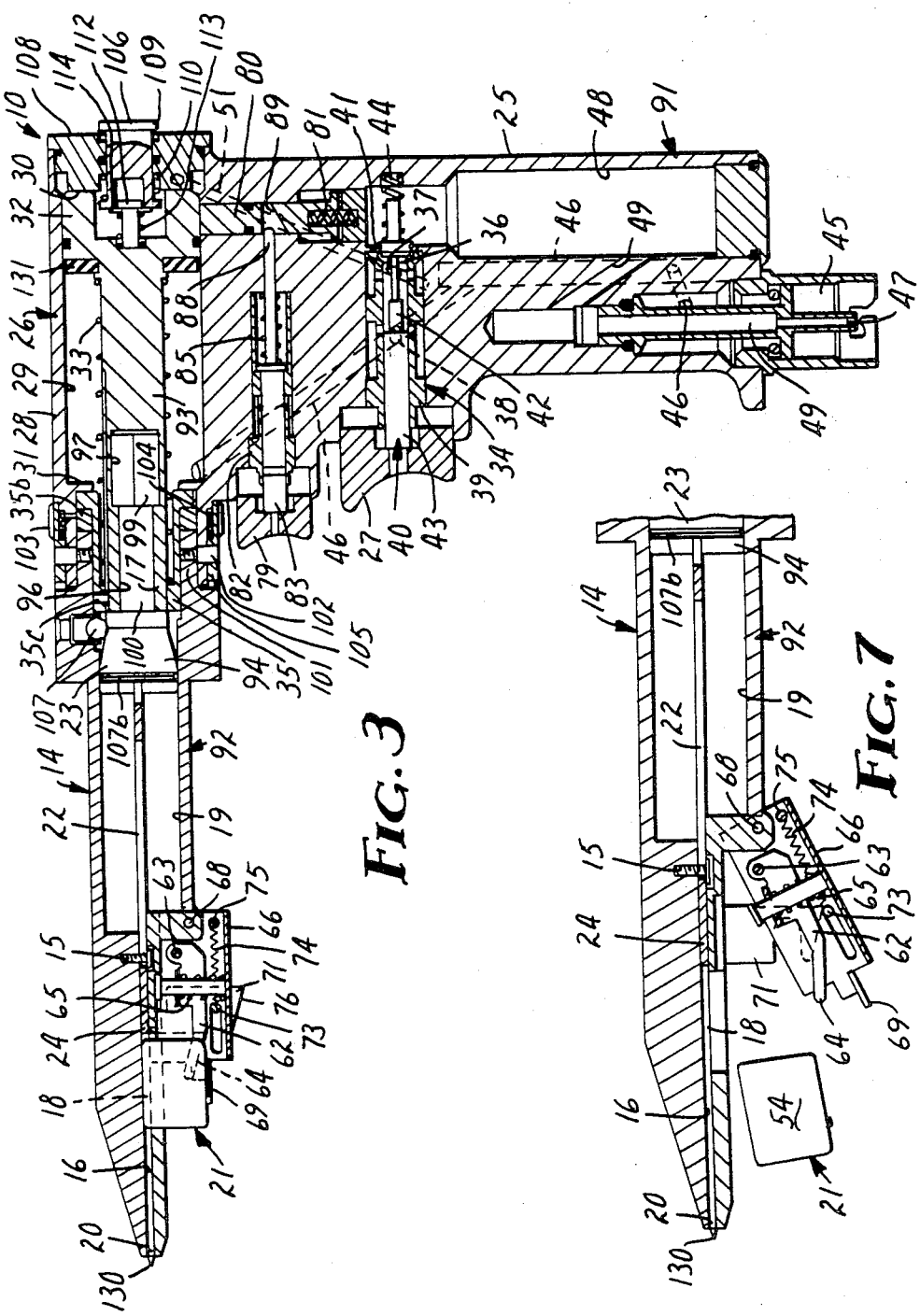

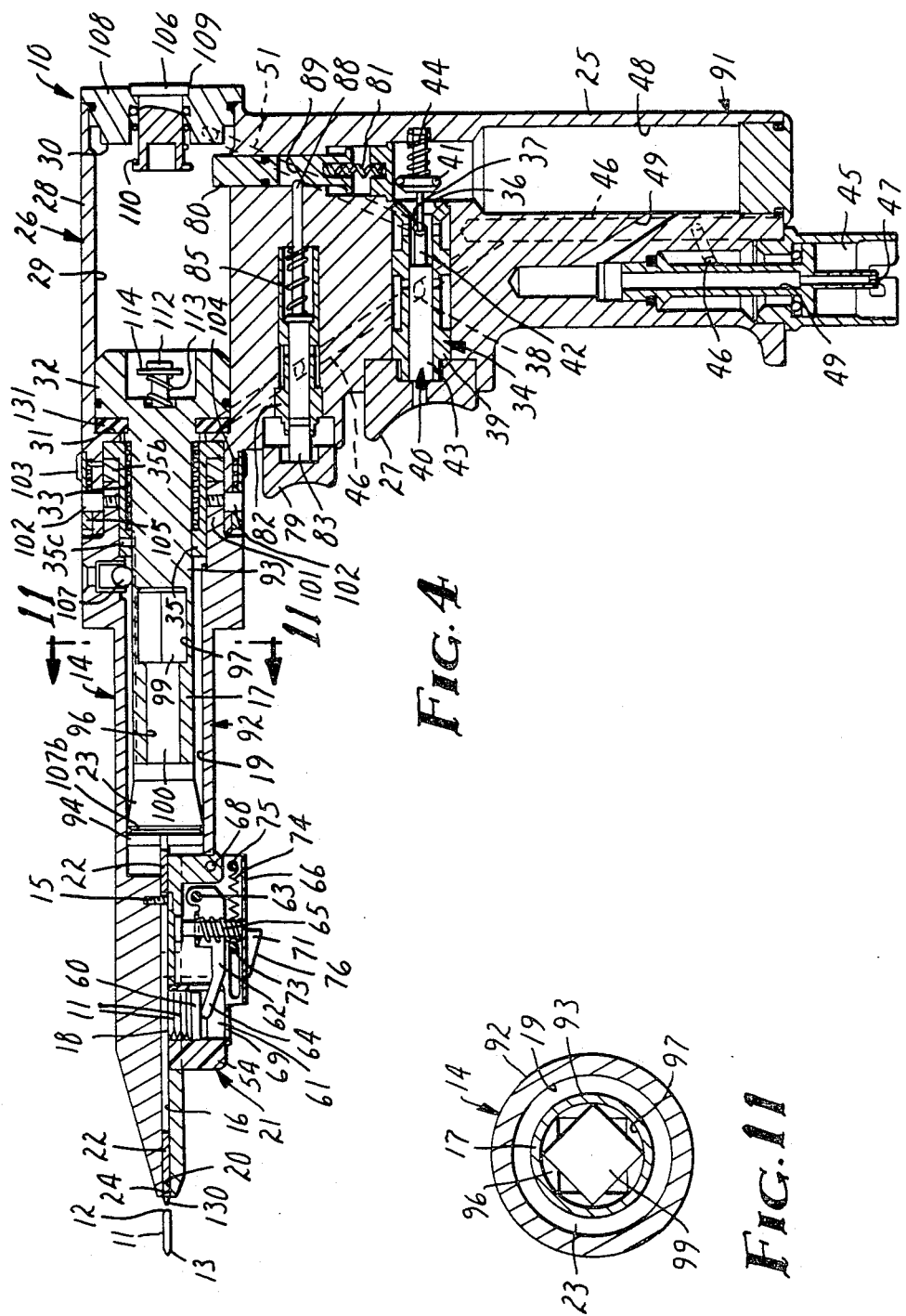

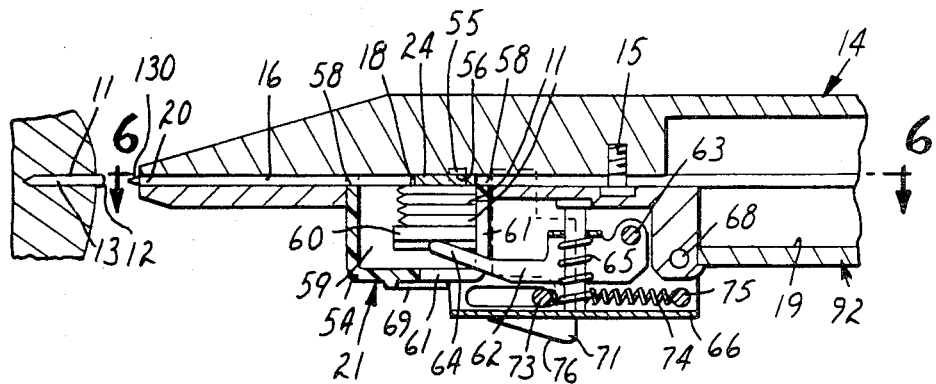
FIG. 5
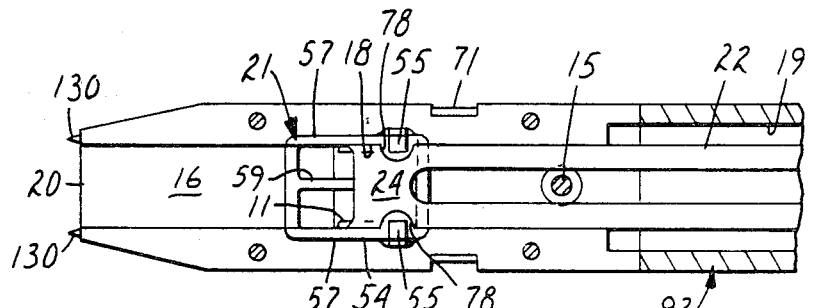
FIG. 6
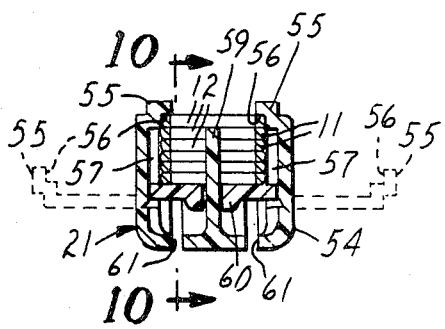
FIG. 9
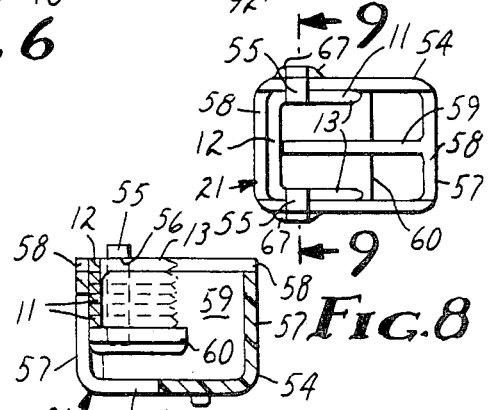
FIG. 8
FIG. 10

BONE STAPLER

TECHNICAL FIELD

This invention relates to devices for driving staples to join adjacent bone portions.

BACKGROUND INFORMATION

Devices are known that facilitate manual hammering of staples into adjacent bone portions, such as is described in U.S. Pat. No. 4,263,903. U.S. Pat. No. 4,414,967 filed June 22, 1981, teaches the use of a stapler that rapidly and reproducibly imparts a controlled amount of energy to propel a staple into bone portions and which provides many advantages over devices of the type described in U.S. Pat. No. 4,263,903. The teachings in that application, however, were based on tests with a commercially available manually actuatable staple gun (i.e., the Model T-50 Staple Gun Tacker manufactured by Arrow Manufacturing Co.) that is impractical for surgical use.

U.S. patent application Ser. No. 508,588, filed June 28, 1983, described the same bone stapling device described in this application which has numerous novel design features which facilitate driving staples into bone portions during surgery. Generally, the bone stapler described in both that application and this application is a stapler of the type adapted for use with generally U-shaped staples each comprising two generally parallel leg portions projecting in the same direction from opposite ends of a central portion. The stapler comprises a housing having a passageway extending from an inlet opening to an outlet opening, which passageway is adapted to guide a single staple moved from the inlet to the outlet opening with distal ends of the leg portions of the staple leading. Means are provided for biasing a stack of staples into the inlet opening, together with a driver having an end portion adapted to engage the central portion of such a staple. The driver is mounted on the housing for sliding movement between a load position spaced from the inlet opening to afford movement of one of the staples into the passageway, along the passageway with the end portion of the driver pushing the staple, and to an eject position at which the end portion of the driver pushes the staple out the outlet opening and at which eject position the driver is stopped. Also drive means adapted to be manually activatable are provided for rapidly and forcefully propelling the driver along the passageway from its load position to its eject position to move a staple from the inlet opening to the outlet opening and drive the staple into portions of bone adjacent the outlet opening.

The novel features claimed in the above mentioned application that singly or collectively particularly adapt the stapler for driving staples into bone portions during surgery include:

(1) A compressed air activated drive means which ensures efficient operation of the stapler while not discharging any air used to operate the stapler adjacent the area at which the staples are applied to thereby restrict contamination of that area. This drive means comprises an air cylinder assembly including a cylinder having first and second ends with a portion of the driver opposite its end portion that engages a staple extending into the second end of the cylinder, which cylinder is partially defined by an inner surface of the housing around and aligned with the driver; and a piston within the cylinder fixed to the driver and in slidable sealing engagement with the inner surface. The piston is movable along the inner surface from a first position adjacent its first end at which it is positioned when the driver is in its load position to a second position adjacent the second end of the cylinder at which it is positioned when the driver is in its eject position. Also included is a valve assembly comprising the housing having a bore and having an inlet port and first and second outlet ports communicating with the bore; and an activator manually movable from a blocking position to which the actuator is biased at which the actuator closes the inlet port and connects the outlet ports, and an activate position connecting the inlet and first outlet ports and closing the second outlet port. The housing has an outlet passageway communicating with the cylinder adjacent its second end and communicating with the second outlet port, which outlet passageway is adapted to be coupled to a hose leading to air at atmospheric pressure remote from the stapler; has an inlet passageway coupled to the inlet port and adapted to be coupled to a source of air under greater than atmospheric pressure, and has a transfer passageway coupled between the first outlet port and communicating with the cylinder adjacent its first end. Thus, when the drive means is activated by moving the actuator to its activate position, air under greater than atmospheric pressure will flow through the inlet and first outlet ports and the transfer passageway to the first end of the cylinder. As the piston starts to move from its first toward its second position under the influence of the high pressure air, air between the piston and the second end of the cylinder will flow out the outlet passageway and through the bore. When the actuator is subsequently returned to its deactivated position the inlet port will be closed, and the first and second outlet ports will be connected so that the high pressure air can escape from the first end of the cylinder by the transfer passageway, the bore and the outlet passageway to the hose, and air at atmospheric pressure as needed can flow to the second end of the cylinder through the outlet passageway.

(2) Means for biasing a stack of staples into the inlet opening comprising a replaceable cartridge. The cartridge includes a case adapted to removably engage the housing and having a slot along one side surface extending generally normal to the passageway, the stack of staples within the case, and a follower on the side of the stack of staples opposite the passageway and movable within the case with the stack of staples. Means are provided for releasably retaining the case in engagement with the housing. A pusher is pivotably mounted on the housing with a distal end portion projecting through the slot and engaging the follower, and means between the pusher and the housing bias the distal end portion of the pusher toward the passageway.

(3) Structure that allows changing one part of the stapler to facilitate driving staples of different sizes. The housing and driver both comprise first and second parts. The first part of the housing defines the inlet and outlet openings and carries the means for biasing, and second part of the housing carries the drive means. Manually actuated engagement means are provided for releasably engaging the first and second parts of the housing and driver to afford using different first parts, each adapted for staples of a different size, with the second parts.

(4) Pointed projections projecting outwardly of the housing and flanking the outlet opening which are adapted to help position and stabilize portions of bone to be joined in the same plane before the staple is driven.

(5) Means for releasably latching the driver in its load position which help ensure that a user cannot unintentionally fire a staple. This means comprises latch means adapted for automatic engagement between the housing and the driver when the driver returns to its load position from its eject position; and a manually activatable button means or botton mounted on the housing for movement from an outer position to which it is biased affording engagement of the latch means, to an inner position engaged with and releasing the latch means to afford movement of the driver to its eject position.

DISCLOSURE OF INVENTION

The novel feature of the bone stapler described above that is claimed in this application is:

(1) Improved structure of the type described above that allows changing first parts of the housing and devices to facilitate driving staples of different sizes. The engagement means comprises one of the parts of the driver having walls defining a socket and the other of the parts of the driver having a tip portion adapted to be inserted in the socket when the parts of the driver are rotated out of alignment and to engage within the walls defining the socket when the parts of the driver are rotated into alignment. Also, the first and second parts of the housing are adapted to be relatively rotated to afford engagement of the driver parts, and means are provided for releasably latching the parts of the housing together in proper alignment.

Also taught in this application are novel features claimed in a separate application filed on even date herewith, which features comprise:

(1) Means for automatically preventing movement of the driver from an intermediate position (at which intermediate position a second staple cannot be fed into the inlet opening of the passageway) to its load position after movement of the driver from its load to its eject position. With this feature, with the driver initially in its load position, the drive means may be manually activated a first time to drive a staple to the outlet opening, and may subsequently be manually activated an additional number of times to further impact that driven staple, as may be desirable to further seat the staple. The stapler further includes manually activated means for resetting this blocking means to allow return movement of the driver from its intermediate to its load position so that a second staple may be driven.

(2) An improved cartridge of the type described above which precludes leaving a staple in the stapler that could be inadvertently driven after the cartridge is removed. The case in this improved cartridge comprises guide wall means defining an inner surface at the end of the stack of staples opposite the follower and side walls projecting normal to the inner surface, which side walls have opposed transverse openings at the inner surface and aligned with the passageway when the cartridge is in the stapler. The inner surface defined by the guide wall means defines a portion of the passageway for the driver at the inlet opening, with the driver being movable through the transverse openings and along the inner surface between its load the eject positions. Thus because all of the staples remain within the cartridge until they are driven, when the cartridge is removed the user can be assured that all staples have also been removed from the stapler.

BRIEF DESCRIPTION OF THE DRAWING

The above and additional novel features will be described with reference to the accompanying drawing wherein like numbers refer to like parts in the several views and wherein:

FIG. 3 is an enlarged sectional view taken along line 3—3 of FIG. 1;

FIG. 4 is an enlarged sectional view taken along line 3—3 of FIG. 1 and similar to FIG. 3, but in which drive means has been activated to drive a staple;

FIG. 5 is an enlarged fragmentary sectional view taken approximately along lines 3—3 of FIG. 1 and similar to FIG. 3 but in which a driver included in the stapler is in an intermediate position;

FIG. 6 is a sectional view taken approximately along line 6—6 of FIG. 5;

FIG. 7 is an enlarged fragmentary sectional view taken approximately along lines 3—3 of FIG. 1 and similar to FIG. 3 except that a staple cartridge is shown separated from the rest of the staples and a cartridge holding mechanism is shown in an open position;

FIG. 8 is an enlarged top view of the cartridge shown separated in FIG. 7;

FIG. 9 is a sectional view taken approximately along line 9—9 of FIG. 8;

FIG. 10 is a sectional view taken approximately along line 10—10 of FIG. 9;

FIG. 11 is an enlarged sectional view taken approximately along line 11—11 of FIG. 4.

DETAILED DESCRIPTION

Figure 1:
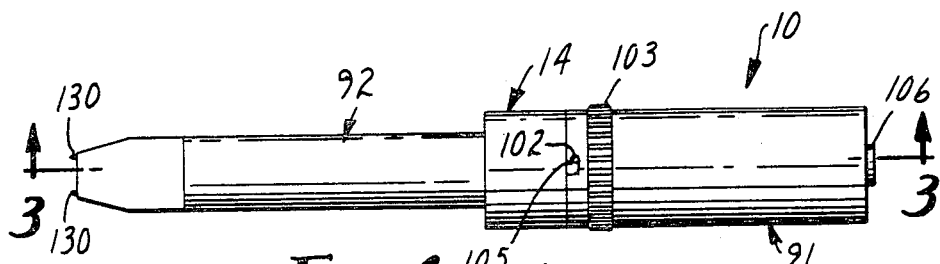
FIG. 1 is a top view of a bone stapler according to the present invention.

Referring now to FIGS. 1 through 10 there is illustrated a bone stapler according to the present invention generally designated by the reference numeral 10.

The stapler 10 is adapted for use with generally U-shaped staples 11 (FIG. 8), each of which staples 11 comprises a central portion 12 and two generally parallel leg portions 13 having pointed distal ends and projecting generally in the same direction from opposite ends of its central portion 12 and preferably diverging by about 1 or 2 degrees so that the driven staple will provide a compressive effect on portions of bone joined by it. Generally the stapler 10 comprises a pistol-shaped housing 14 having a passageway 16 (FIGS. 3 through 6) extending from an inlet opening 18 to an outlet opening 20, which passageway 16 is adapted to guide one of the staples 11 from the inlet opening 18 to the outlet opening 20 with the distal ends of the staple 11 leading. Means are provided for biasing a stack of the staples 11 contained in a replaceable cartridge 21 into the inlet opening 18. A driver 22 having an end portion 24 adapted to engage the central portion 12 of one of the staples 11 is mounted on the housing 14 for sliding movement between a load position (FIG. 3) with the driver 22 spaced from the inlet opening 18 to afford movement of one of the staples 11 into the passageway 16, along the passageway 16 with its end portion 24 pushing the staple, to an eject position (FIG. 4) at which the end portion 24 of the driver 22 pushes the staple 11 out of the outlet opening 20 and at which eject position the driver 22 is stopped. Drive means including an air cylinder assembly 26 powered by air under greater than atmospheric pressure and adapted to be manually activated by pulling a actuating trigger 27 into a handle-portion 25 of the housing 14 are provided for rapidly and forcefully propelling the driver 22 along the passageway 16 from the load position to the eject position to move the staple 11 from the inlet opening 18 to the outlet opening 20.

The driver 22 comprises a longitudinally slotted blade-like portion on which its end portion 24 is formed and which is guided along the housing 14 by a headed pin 15 fixed in the housing 14 that projects through the slot in the blade-like portion. Also included in the driver 22 is a cylindrical portion 17 that moves within a cylindrical guide bore 19 in the housing 14, to which cylindrical portion 17 the blade-like portion is attached at a frustro conical end plug 23 that slides in close-fitting engagement in the guide bore 19.

The drive means for propelling the driver 22 comprises the air cylinder assembly 26 which includes a cylinder 28 partially defined by a cylindrical inner surface 29 of the housing 14 concentric with the guide bore 19, which inner surface 28 has first and second ends 30 and 31, and a piston 32 within the cylinder 28 integral with an end portion of the driver 22 opposite its end portion 24. The piston 32 is in slidable sealing engagement with the cylindrical inner surface 29, and is movable along the inner surface 29 between a first position adjacent the first end 30 of the cylinder 28 at which the piston 32 is located when the driver 22 is in its load position and to which the piston 32 is biased by a main spring 33 within the piston 32 and the housing 14; and a second position adjacent the second end 31 of the cylinder 28 at which the piston 32 is positioned when the driver 22 is in its eject position.

The end of the main spring 33 opposite the piston 32 is supported against an annular inwardly projecting ledge on a guide collar 35 which guide collar 35 has an outwardly projecting rim fixed against an inwardly projecting lip in the housing 14 by an anchor ring 35b threadably engaged with the housing 14. The inner surface of the inwardly projecting ledge is in close engagement around the driver 22 and carries a pin 35c positioned in a longitudinal groove in the driver 22 to allow longitudinal movement of the driver 22 between its load and eject positions while the pin 35c prevents rotation of the driver 22 relative to the housing 14.

The actuating trigger 27 by which the air cylinder assembly 26 is actuated is included in a valve assembly 34 comprising the housing having a bore opening through the front of its handle portion 25 in which a guide spool 39 is fixed and having an inlet port 36 and first and second outlet ports 37 and 38 communicating with the bore. An actuator 40 coupled to the actuating trigger 27 by a set screw (not shown) is manually movable within the guide spool 39 from an outer blocking position (FIG. 3) at which an O-ring 41 around a groove in the actuator 40 engages a seat around and closes the inlet port 36, and clearance between a small diameter portion 42 of the actuator 40 and the inner surface of the guide spool 39 connects the outlet ports 37 and 38 through transverse passageways in the guide spool 39; and an inner activate position (FIG. 4) with the O-ring 41 separated from the seat to connect the inlet port 36 and the first outlet port 37 past the small diameter portion 42 of the actuator 40, and at which a larger diameter 43 portion of the actuator 40 essentially closes the transverse passageways in the guide spool 39 leading to the second outlet port 38. A spring 44 provides means for biasing the actuator 40 to its outer blocking position, against which spring 44 the actuator 40 may be manually moved or pulled to its activate position by the actuating trigger 27. The housing 14 has an outlet passageway 46 which communicates with the cylinder 28 adjacent its second end 31, communicates with the second outlet port 38, and is adapted to be coupled to a portion of a hose (not shown) leading to air at atmospheric pressure through a conventional surgical air inlet connector, a female half 45 of which is formed in the housing 14. The housing 14 also has an inlet passageway 47 including an enlarged reservoir portion 48 (which provides sufficient air volume to quickly move the piston 32) coupled to the inlet port 36 and a smaller portion 49 adapted to be coupled to a source of air under greater than atmospheric pressure through the female coupling half 45. Also included is a transfer passageway 51 coupled between the first outlet port 37 and communicating with the cylinder 28 adjacent its first end 30. Thus, when the stapler 10 is activated by the actuating trigger 27 being pulled into the housing 14 to move the actuator 40 to its activate position (FIG. 4), air under greater than atmospheric pressure in the reservoir 48 and from the supply will flow through the inlet port 36, past the small diameter actuator portion 42 and out the transfer passageway 51 to the first end 30 of the cylinder 28, while the larger diameter portion 43 of the actuator 40 precludes any significant amount of the high pressure air from escaping into the outlet passageway 46. As the piston 32 starts to move from its first to its second position under the influence of the high pressure air, air between the piston 32 and the second end 31 of the cylinder 28 will flow out the outlet passageway 46 and to the atmosphere through a hose (not shown) coupled at the female coupling half 45. When the actuating trigger 27 is subsequently released (FIG. 3), the actuator 40 will return to its deactivate position under the influence of the spring 44 so that the inlet port 36 is closed, and the first and second outlet ports 37 and 38 are connected past the small diameter portion 42 of the actuator 40 so that the high pressure air can escape from behind the piston 32 via the transfer passageway 51, bore 35 and outlet passageway 46, and air at atmospheric pressure as needed can flow to the front of the piston 32 via the outlet passageway 46.

The means for biasing the stack of staples 11 into the inlet opening 18, best seen in FIG. 5, comprises the cartridge 21 which is releasably received in the housing 14 and includes a case 54 comprising a pair of opposed hook-like projections 55 providing guide wall means defining an inner surface 56 at one end of the stack of staples 11, and side walls 57 projecting normal to the inner surface 56. The side walls 57 have opposed transverse openings 58 adjacent the inner surface 56 and aligned with the passageway 16 when the cartridge 21 is engaged in the housing 18 so that the inner surface 56 defines a portion of the passageway 16 at its inlet opening 18, and so that the driver 22 is movable through the transverse openings 58 and along the inner surface 56 between its load and eject positions. The cartridge 21 further includes a follower 60 on the side of the stack of staples 11 opposite the inner surface 56 and passageway 16 and guided along a central rib 59 included in the case 54, which follower 60 is movable within the case 54 with the stack of staples 11. One of the side walls 57 of the case 54 has a pair of longitudinal slots 61 disposed generally at a right angle to the passageway 16 and the transverse openings 58. A pusher 62 has one end portion pivotably mounted on a retaining bracket 66 (included in the means for releasably retaining the cartridge 21 on the housing 14 as will later be explained) at a pin 63 and has two opposite distal end portions 64 projecting through the longitudinal slots 61 and in engagement with the side of the follower 60 opposite the stack of staples 11. Means in the form of a spring 65 is provided for biasing the distal end portions 64 of the pusher 62, and thus the stack of staples 11, toward the projections 55. Thus as the driver 22 moves through the transverse openings 58 and along the inner surface 56 defined by the projections 55 during movement from its load to its eject position, the driver 22 will carry with it the staple 11 pressed against the inner surface 56 by the follower 60, pusher 62 and spring 65. When removed, the cartridge 21 will carry with it all of the staples 11 remaining in the stapler 10 so that with the cartridge 21 removed it will be impossible to inadvertently fire a staple 11 from the stapler 10.

The hook-like projections are preferably integrally molded with the case 54 in positions projecting at about right angles to side walls 57 of the case 54 as is shown in dotted outline in FIG. 9, and are then pivoted and frictionally pressed into grooves between rails 67 molded along the side walls 57 (see FIG. 8) to their opposed positions described above.

The means for releasably retaining the cartridge 21 in the housing 14 comprises a socket in the housing 14 adapted to closely conform to and receive an end portion of the case 54 including the opposed projections 55 to key the proper location of case 54 in the housing 14 with its inner surface 56 aligned with one side of the passageway 16, and the retaining bracket 66 which is pivotably mounted on the housing 14 at a pin 68 for manual movement between a closed position (FIGS. 2 through 5) at which a transverse ledge 69 on the retaining bracket 66 engages the end of the case 54 opposite the housing 14 and holds the case 54 in the socket and at which the pusher 62 carried by the bracket 66 is biased against the follower 60 by the spring 65; and an open position (FIG. 7) with the ledge 69 spaced from the cartridge 21 when it is in the socket to afford removal or insertion of the cartridge 21 with respect to the socket. Means are also provided for releasably retaining the retaining bracket 66 in its closed position, comprising a pair of hook like members 71 fixed to the housing 14 flanking the retaining bracket 66 and defining slots opening toward the front end of the housing 14; and a transverse rod 73 slideably mounted in spaced slots in the retaining bracket 66 for movement between an inner position (to which the rod 73 is based by a spring 74 between the rod 73 and an anchor pin 75 on the retaining bracket 66) and an outer position at the end of the slots opposite the anchor pin 75. When the retaining bracket 66 is in its closed position and the rod 73 is in its inner position, engagement of the rod 73 with the slots in the hook like members 71 will hold the retaining bracket 66 in its closed position. Manual movement of the rod 73 to its outer position against the bias of the spring 74 will afford pivoting of the retaining bracket 66 from its closed to its open position. Subsequent movement of the retaining bracket 66 from its open toward its closed position will cause the rod 73 to move toward its outer position along caming surfaces 76 defined along the distal edges of the hook-like members 71 until the rod 73 again engages the slots in the hook-like member 71 to hold the retaining bracket 66 closed.

The bone stapler 10 also includes blocking means for automatically preventing movement of the driver 22 to its load position from an intermediate position between its load and eject positions with a portion of the driver 22 projecting partially through the cartridge 21 and across the inlet opening 18 to passageway 16 (FIGS. 5 and 6) after the driver 22 has moved from its load to its eject position. Thus, with the driver 22 initially in its load position, the drive means may be manually activated a first time by pulling the actuating trigger 27 to drive a staple 11 through the outlet opening 20 and may subsequently be manually activated an additional number of times by pulling the actuating trigger 27 so that the driver 22 will be again propelled to its eject position to further impact that driven staple 11 as may be needed to fully seat the driven staple 11, without driving an additional staple 11 from the cartridge 21. Also included are reset means manually activated by a reset member or trigger 79 for resetting the blocking means to allow return movement of the driver 22 from its intermediate to its load position so that another staple 11 may be driven. Even with the driver 22 in its intermediate position extending partially through the cartridge 21, the cartridge 21 may be removed and replaced. The driver 22 has arcuate notches 78 along its sides (FIG. 6) that align with the projections 55 when the driver 22 is in its intermediate position to allow the projections 55 to be withdrawn from the cartridge 21 receiving socket in the housing 14 through the notches 78.

The blocking means in the bone stapler 10 comprises a plunger 80 axially slidably mounted in a bore in the housing 14 communicating with the cylinder 28 at its first end 30 for movement in a direction normal to the axis of the cylinder 28 between a nonblocking position (FIG. 3) spaced from within the cylinder 28, to a blocking position (FIG. 4) partially within the cylinder 28 to which the plunger 80 is biased by a spring 81, so that engagement between the plunger 80 and the side of the piston 32 adjacent the first end 30 of the cylinder 28 will define the intermediate position for the piston 32. When the piston 32 is in its first position corresponding to the load position of the driver 22, the periphery of the piston 32 will retain the plunger 80 in its non-blocking position in opposition to the biasing of the spring 81 (FIG. 3). Upon movement of the piston 32 from its first position toward its second position corresponding to the eject position of the driver 22, however, the plunger 80 will automatically move to its blocking position under the influence of the spring 81 (FIG. 4) to thus preclude the piston 32 from returning to its first position and thus preclude the driver 22 from returning to its load position until the reset means is operated by the reset trigger 79.

The reset means comprises the reset trigger 79 fastened by a set screw (not shown) to an outer end portion of a spindle 83, which spindle 83 is slidably mounted in a sleeve 82 fixed in a bore opening through the front of the handle portion 25 of the housing 14 for longitudinal sliding movement between an outer position (FIGS. 3 and 4) and an inner position (not shown). Also included in the reset means are means in the form of a spring 85 for biasing the reset trigger 79 to its outer position, and cam means on the spindle 83 and reset trigger 79 for moving the plunger 80 from its blocking to its nonblocking position against the bias of spring 81 upon manual movement of the spindle 83 from its outer to its inner position via the re-set trigger 79. The cam means comprise a semispherical tip 88 on the inner end of the spindle 83, and a surface 89 inclined with respect to the axis of the spindle 83 partially defining a slot in the plunger 80 in which the tip 88 is received to prevent rotation of the plunger 80. The slot in the plunger 80 is sufficiently long to afford movement of the plunger 80 from its nonblocking to its blocking position under the influence of the spring 81 after the driver moves toward its eject position. With the plunger 80 in its blocking position the reset trigger 79 may be manually pulled toward the handle portion 25 of the housing 14 which will cause the tip 88 to engage the inclined surface 89 so that the plunger 80 will be pulled back to its nonblocking position. This will allow the piston to return to its first position, and cause the driver 22 to return to its load position under the influence of the main spring 33.

The bone stapler 10 is designed to afford driving staples of different sizes in that it is made in two separable assemblies including a handle assembly 91 which includes the drive means mounted on one part of the housing 14, and a barrel assembly 92 which defines the passgeway 16 and receives the cartridge 21 for staples 11 of one size on another part of the housing 14. Means are provided for releasably engaging the parts of the housing 14, and the driver 22 is separable into a second part 93 included in the handle assembly 91 and connected to the piston 32, and a first part 94 including its end portion 24 which is included in the barrel assembly 92. Different barrel assemblies that each have a housing part defining a passageway, a driver part and accept cartridges of a different size of staple may be substituted for the barrel assembly 92 to afford driving stapler of different sizes.

Means are provided for releasably engaging the first and second parts 94 and 93 of the driver 22 and for releasably engaging the handle and barrel assemblies 91 and 92. These means comprise walls on the first part 94 of the driver 22 opposite its end portion 24 defining a socket with an outer portion 96 having a square cross section and an inner portion 97 with a circular cross section; and a tip on the first part 94 of the driver 22 including a distal square portion 99 adapted to slide within the socket through its outer portion 96 and to rotate in its inner portion 97 out of alignment with the outer portion 96 (see FIG. 11) with the walls defining the outer portion 96 around a reduced diameter cylindrical portion 100 of the drivers first part 94. The part of the housing 14 included in the barrel assembly 92 includes a collar 101 at its end opposite the outlet opening 20 received in a socket in the part of the housing 14 included in the handle assembly 91 with the square portion 88 of the tip out of alignment with the outer portion 96 of the wall defining the socket, with four evenly spaced radially outwardly projecting pins 102 fixed on the collar 101 received in four longitudinally extending slots opening through the end of the housing part included in the handle assembly 91, and with hooks 105 on a ring 103 mounted for rotation about its axis on the housing part included in the handle assembly 91 in engagement with the pins 102 to releasably latch the handle and barrel assemblies 91 and 92 together. The barrel assembly 92 can thus be located at different orientations displaced 90 degrees from each other with respect to the handle assembly 91 to provide various orientations of a driven staple 11 relative to the handle portion 25 of the housing 14. To release the handle and barrel assemblies 91 and 92 from each other, the ring 103 is rotated against the bias of a coil spring 104 to move the hooks 105 from around the pins 102. The handle and barrel assemblies 91 and 92 are pulled apart axially of the driver 22 which pulls the pins 102 from the slots in which they are received and pulls the part of the housing 14 on the barrel assembly 92 along the driver 22 until the headed pin 15 reaches the end of the slot in the driver 22, at which position a spring loaded ball 107 carried by the housing part on the barrel assembly engages a groove 107b around the end plug 23, which engagement will keep the end plug 23 from moving into the guide bore 19 after the handle and barrel assemblies 91 and 92 are separated. The handle and barrel assemblies 91 and 92 are then rotated about 45 degrees relative to each other about the axis of the driver 22 to align the square position 99 of the tip with the outer portion 96 of the socket, whereupon the tip may be pulled from the socket and the assemblies 91 and 92 may be separated. Reengagement of the handle and barrel assemblies 91 and 92 is accomplished by reversing the steps listed above. Upon pressing the pins 102 into the slots, camming surfaces 105b on the hooks 105 will cause the collar 101 to automatically rotate to engage the hooks 105 around the pins 102.

The bone stapler 10 also includes means for indicating to a user ready to fire the stapler 10 whether the driver 22 is in its load position from which a staple 11 can be driven or in its intermediate position. An indicating spool 106 is centrally slidably mounted in a removable plug 108 providing a portion of the housing 14 at the first end 30 of the cylinder 28. The indicating spool 106 is slidable between an inner position with a flange 109 at its outer end against the outer surface of the plug 108 to which the indicating spool 106 is biased by a spring 110, and an outer position with a portion of the spool 106 adjacent the flange 109, which is painted red, projecting from the plug 108. The piston 32 carries a central headed pin 112 at its end adjacent the first end 30 of the cylinder 28 around which pin 112 is a slidable washer 114 biased against the head of the pin 112 by a spring 113 with a greater spring constant than the spring 110. When the driver 22 is in its load position, the head of the pin 112 will enter an opening in the spool 106 while the washer 114 will be pressed against the adjacent end of the indicating spool 106 under the influence of the spring 113 causing the spool 106 to move to its outer position at which its red periphery indicates that the driver 22 is in its load position. When the driver 22 moves away from its load position, the indicating spool 106 will move to its inner position under the influence of the spring 110, thereby indicating to a user that the driver 22 is in its intermediate position.

Figure 2:
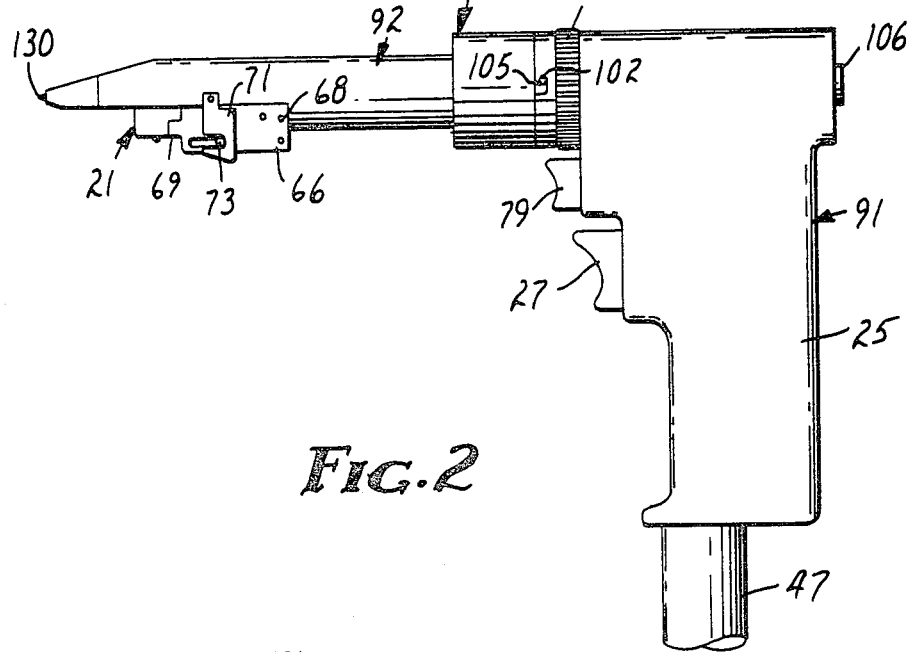
FIG. 2 is a side view of the bone stapler of FIG. 1.
Figure 12:
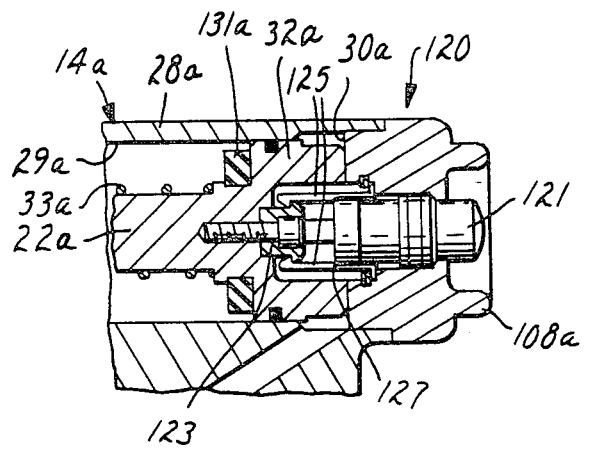
FIG. 12 is a sectional view showing a safety button assembly that could be substituted for an indicator assembly illustrated in FIG. 1.

Referring now to FIG. 12 there is shown a safety means that could be incorporated in a bone stapler 120 instead of the indicating means including the indicating spool 106 shown in FIG. 2. In describing this safety means, portions of the stapler 120 that are essentially the same as corresponding portions of the stapler 10 will be identified by the same reference numeral to which has been added the suffix "a".

The safety means includes means for releasably latching a piston 32a at a first end 30a of a cylinder 28a to thereby lock a driver 22a in its load position. The safety means comprises latch means adapted for automatic engagement between a housing 14a and the piston 32a when the driver 22a returns to its load position from its eject position, manually activatable button means including a button 121 mounted on the housing 14a for axial sliding movement from an outer position affording engagement of the latch means to an inner position engaged with and releasing the latch means to afford movement of the driver 22a to its eject position, and means provided by air pressure in the cylinder 28a for biasing the button 121 to its outer position.

The latch means comprises a headed pin 123 projecting centrally from the end of the piston 32a adjacent the first end 30a of the cylinder 28a, and two pairs of resiliently flexible opposed cantilevered hooks 125 disposed in a circular array, having one end fixed on the plug 108a, and projecting toward the pin 123. Distal camming surfaces on the pin 123 and hooks 125 are shaped to cause resilient outward deflection and engagement of the hooks 125 over the head of the pin 123 when the piston 32a returns to its first position corresponding to the load position of the driver 22a. Such engagement will prevent movement of the piston 32a that would cause movement of the driver 22a to its eject position even when the drive means (not shown) is activated by pulling a main trigger. The latch means can be released, however, by manually pressing the button 121 inwardly so that a cam surface 127 on the inner end of the button 121 will engage and separate the hooks 125, moving them radically out of engagement with the head of the pin 123, whereupon the driver may be moved to drive a staple by pulling the main trigger to activate the drive means.

OPERATION

The operation of the bone stapler 10 by a user will now be described assuming that a cartridge 21 containing a stack of staples 11 is held in the housing 14 by the retaining bracket 66 and the stapler 10 is connected at the coupling half 45 to a hose assembly (not shown) including a central supply of air under greater than atmospheric pressure coupled to the inlet passageway 47 and an outer hose leading to air at atmospheric pressure coupled to the outlet passageway 46. The user can utilize a pair of pointed locating members 130 fixed to the housing 14 in positions flanking the outlet opening 20 and projecting generally parallel to the axis of the driver 22 to help position and stablize bone portions to be stapled in the same plane. When the bone portions are thus positioned, the stapler 10 can be activated by manually pulling the actuating trigger 27 so that air under greater than atmospheric pressure is coupled through the reservoir 48, valve assembly 34 and transfer passageway 51 to the first end 30 of the cylinder 28 which will cause rapid movement of the piston 32 and thereby the driver 22 from its load position spaced from the staple inlet opening 18, and through the cartridge 21 along its inner surface 56 to push the adjacent staple 11 in the stack along the passageway 16 to the outlet opening 20 and drive that staple 11 into adjacent portions of bone, the driver 22 being stopped at its eject position at the outlet opening 20 by engagement of the piston 32 with a rubber collar 131 at the second end 31 of the cylinder 28. As the piston 32 thus is moved away from the first end 30 of the cylinder 28, the plunger 80 will move into the cylinder 28 under the influence of the spring 81 so that, after the actuating trigger 27 is released and the high pressure air at the first end 30 of the cylinder 28 escapes through the transfer passageway 51, valve assembly 34 and outlet passageway 46 to the hose coupled to atmospheric pressure and the piston 32 moves back toward its first position under the influence of the main spring 33, the piston will be stopped against the periphery of the plunger 80 with the end portion 24 of the driver 22 at an intermediate position extending through the cartridge 21 so that the next staple 11 in the stack of staples 11 can not move into the inlet opening 18 to the passageway 16. The user, if desired, can then again rapidly move the driver 22 to its eject position by again pulling the actuating trigger 27 as may be desired to further, drive or seat the staple 11 previously driven into the bone portions.

When the user desires to drive a second staple 11, he can pull the re-set trigger 79 which will move the tip 88 of the spindle 83 against the inclined surface 89 to cam the plunger 80 out of the cylinder 28 to its non-blocking position so that the main spring 33 can return the piston 32 to its first position and thereby the driver 22 to its load position allowing the uppermost staple 11 in the cartridge 21 to move against the inner surface 56 of the cartridge 21 at the inlet opening 18 so that subsequent activation of the drive means by the actuating trigger 27 will drive that staple 11.

If the user wishes to remove the cartridge 21 because it is empty, or to insure that the stapler 10 can not fire another staple 11, or to insert staples with different length leg portions 13, he may do so by manually retracting the rod 73 out of the slots in the hook-like portions 71 against the bias of the spring 74, and pivoting the retaining bracket 66 from its closed position (FIGS. 2 through 5) to its open position (FIG. 7) so that the cartridge 21 can be removed from the socket in the housing 14. He can then be sure that no staples 11 remain in the stapler 10, since the entire remaining stack of staples 11 (if any) remains in the cartridge 21. The same or a new cartridge 21 of staples 11 may again be loaded into the stapler 10 by inserting the cartridge 21 into the socket in the housing 14 and moving the retaining bracket 66 to its closed position, which will cause the rod 73 to move along the caming surfaces 76 of the hook-like portions 71 and subsequently into the slots therein to hold it closed.

If the user wishes to drive staples of a different width along its central portion 12, he may also do that by substituting an appropriate different barrel assembly for the barrel assembly 92 being used, which different barrel assembly is adapted to accomodate staples 11 of that width. Such substitution is easily accomplished by rotating the locking collar 103 to release the two parts of the housing 14, pulling and relatively rotating the housing parts with respect to the longitudinal axis of the driver 22 (as is described in greater detail above) which will cause the square portion 99 on the first part 94 of the driver 22 to align with the square cross section portion 96 of walls defining the socket in the second part 93 of the driver 22 in which the square portion 99 is received, and pulling the first and second parts of the housing 14 and driver 22 away from each other to pull the square portion 99 from the socket and separate them. The different barrel assembly can then be assembled on the handle assembly 91 by reversing the separating steps.

The present invention has now been described with reference to one embodiment and one modification thereof. It will be appreciated that many modifications and changes can be made in the structure of the bone stapler 10 without departing from the spirit of the present invention, and that effective bone stapler can be made that incorporate only one or different combinations of the inventive features described and claimed herein. Thus the scope of the claims in this application should not be limited by the structure of the stapler described herein, but only by the structures described by the language of the claims and their equivalents.

I claim:

1. A bone stapler adapted for use with generally U-shaped staples each comprising a central portion and two generally parallel leg portions projecting generally in the same direction from opposite ends of its central portion and having distal ends, said stapler comprising:

a housing having a passageway extending from an inlet opening to an outlet opening, said passageway being adapted to guide a single staple moved from the inlet to the outlet opening with the distal ends of its legs leading;

means for biasing a stack of staples into said inlet opening;

a driver having an end portion adapted to engage the central portion of a said staple and being mounted on said housing for sliding movement between a load position with the driver spaced from the inlet opening to afford movement of one of the staples into the passageway, along said passageway through an intermediate position with said end portion pushing the staple, to an eject position at which the end portion of the plunger pushes the staple out said outlet opening and at which eject position the driver is stopped by said housing, said driver having a length along said passageway so that a portion thereof will be positioned adjacent said inlet opening during movement of said ram from said intermediate to said eject position to prevent movement of a second staple in said stack into said passageway through said inlet opening; and drive means adapted to be manually activatable for rapidly and forcefully propelling said driver along said passageway toward said eject position and for subsequently biasing said driver for movement from said eject position back to said load position;

said housing and driver both comprising first and second parts, said first part of said housing defining said inlet and outlet openings and carrying said means for biasing, and said second part of said housing carrying said drive means; and said stapler including manually operable engagement means adapted for releasable engagement to afford using first parts adapted for staples of different sizes with said second part, said engagement means comprising one of said parts of said driver having walls defining a socket and the other of said parts of said driver having a tip portion adapted to be inserted in said socket when said parts of said driver are rotated out of alignment and to engage within said walls when said parts of said driver are rotated into alignment; said parts of said housing being adapted to be relatively rotated to afford engagement of said driver parts, and means adapted for releasably latching said parts of said housing together in proper alignment.

* * * * *